US00PP37082P2

(12) United States Plant Patent
Choi

(10) Patent No.: US PP37,082 P2
(45) Date of Patent: Nov. 4, 2025

(54) STRAWBERRY PLANT VARIETY NAMED 'Gold Berry'

(50) Latin Name: ***Fragaria* x *ananassa***
Varietal Denomination: Gold Berry

(71) Applicant: FarmyirehSe Co., Ltd., Seoul (KR)

(72) Inventor: Iyeong Choi, Seoul (KR)

(73) Assignee: FarmyirehSe Co., Ltd., Seoul (KR)

( * ) Notice: Subject to any disclaimer, the term of this patent is extended or adjusted under 35 U.S.C. 154(b) by 0 days.

(21) Appl. No.: 18/963,927

(22) Filed: Nov. 29, 2024

(51) Int. Cl.
*A01H 5/08* (2018.01)
*A01H 6/74* (2018.01)

(52) U.S. Cl.
USPC ..... Plt./208

(58) Field of Classification Search
USPC ..... Plt./208, 209
CPC ..... A01H 5/08; A01H 5/00; A01H 6/7409; A01H 6/74
See application file for complete search history.

(56) References Cited

U.S. PATENT DOCUMENTS

PP29,729 P2 10/2018 Kibbe et al.
PP31,609 P2 3/2020 Geoghegan
PP32,800 P3 2/2021 Larse
PP34,242 P2 5/2022 Knapp et al.
PP34,265 P2 5/2022 Knapp et al.
11,419,301 B2 8/2022 Larse

OTHER PUBLICATIONS

Damyang-Gun, Certificate of Protection and Report for Strawberry 'Merryqueen,' PVPO No. 202200641, US Plant Variety Protection Office, The United States of America, 26 pages (Jan. 2024).
Gyeongsangnam-do Agricultural Research & Extension Services, Certificate of Protection and Application for Strawberry '*Kuemsil*,' PVPO No. 202100367, US Plant Variety Protection Office, The United States of America, 17 pages (Jan. 2023).
International Union for the Protection of New Varieties of Plants, "Strawberry, UPOV Code(s): Fraga, *Fragaria* L.," Guidelines for the Conduct of Tests for Distinctness, Uniformity, and Stability, Geneva, Switzerland, 40 pages (Aug. 2023).
Mie Prefecture, Kagawa Prefecture, Chiba Prefecture, National Agricultural and Food Research Organization (NARO), Certificate of Protection and Application for Strawberry '*Yotsuboshi*,' PVPO No. 201800224, US Plant Variety Protection Office, The United States of America, 31 pages (May 2020).
Hetero, Publication of Plant Variety Protection Application for Strawberry '*Gold berry*,' Appln. No. 2023-79, Korea Seed & Variety Service, Republic of Korea, 4 pages (Mar. 2023).

*Primary Examiner* — June Hwu
(74) *Attorney, Agent, or Firm* — Sterne, Kessler, Goldstein & Fox P.L.L.C.

(57) ABSTRACT

A new and distinct variety of strawberry plant named 'Gold Berry' particularly characterized by its large and hard-skinned fruits, is disclosed.

6 Drawing Sheets

Botanical classification: *Fragaria* x *ananassa*.
Varietal denomination: 'Gold Berry'.

BACKGROUND OF THE INVENTION

Strawberry (*Fragaria* x *ananassa*) is one of the most important horticultural crops worldwide. In 2022, global strawberry production reached approximately 9,569,864 tonnes, covering a cultivation area of 397,603 hectares (Food and Agriculture Organization of the United Nations, 2022). Strawberries are primarily cultivated for their fruit, which is consumed fresh or processed into products such as jams, juices and other goods. The fruit of strawberry plants can vary in size, shape, firmness, and sweetness, often depending on the cultivar producing the fruit.

Accordingly, there is a need for new varieties of strawberry plants. In particular, there is a need for improved varieties of strawberry plant that yield large, high sugar content fruit with a long shelf life.

SUMMARY OF THE INVENTION

The present invention is directed to a new and distinct cultivar of *Fragaria*, botanically known as *Fragaria* x

*ananassa*, having the common name of strawberry, and hereinafter referred to by its variety denomination 'Gold Berry'.

The variety was first cultivated in 2019 and originated by means of conventional breeding from a cross between the proprietary female parent 'H2K-06' (unpatented) and the proprietary male parent 'STC-18-22' (unpatented) by the inventor at the premises of Dongsan-ri, Galsan-myeon, Hongseong-gun, Chungcheongnam-do, Republic of Korea. Large-fruit bearing & high-yield variety H2K-06 was crossed with high-sweetness and higher firmness variety STC-18-22. This cross initially yielded 600 child varieties. Out of the 600 child varieties, 580 were tested for desired traits and further developed throughout 2020-2021. In 2021 the variety with the highest desired quality was identified as 'Gold Berry' and its stability was affirmed in 2022 by asexual propagation via stolons at the premises of Dongsan-ri, Galsan-myeon, Hongseong-gun, Chungcheongnam-do, Republic of Korea.

Continued rounds of asexual propagation of 'Gold Berry' via stolons confirms that the present invention is stable and uniform.

'Gold Berry' exhibits many distinctive characteristics when grown under normal horticultural practices in Dongsan-ri, Galsan-myeon, Hongseong-gun, Chungcheongnam-do, Republic of Korea. 'Gold Berry' is characterized by its large, vivid red fruit with a touch of gold-orange color to the fruit flesh when the fruit is ripe. The fruit of 'Gold Berry' has a conical shape, and is symmetrical throughout its longitudinal axis. The fruit of 'Gold Berry' is also characterized by its long shelf-life, due in part to its high firmness and hard skin. 'Gold Berry' fruit are also characterized by high sweetness and excellent scent, including during cold storage of harvested fruit. 'Gold Berry' was selected for its large, high-sugar content fruit with a long shelf life.

BRIEF DESCRIPTION OF THE DRAWINGS

This new and distinctive strawberry plant is illustrated by the accompanying photographs which show fruit, flowers, and leaves of the plant. The colors shown are as true as can be reasonably obtained by conventional photographic procedures.

DETAILED BOTANICAL DESCRIPTION OF THE PLANT

Figure 1:
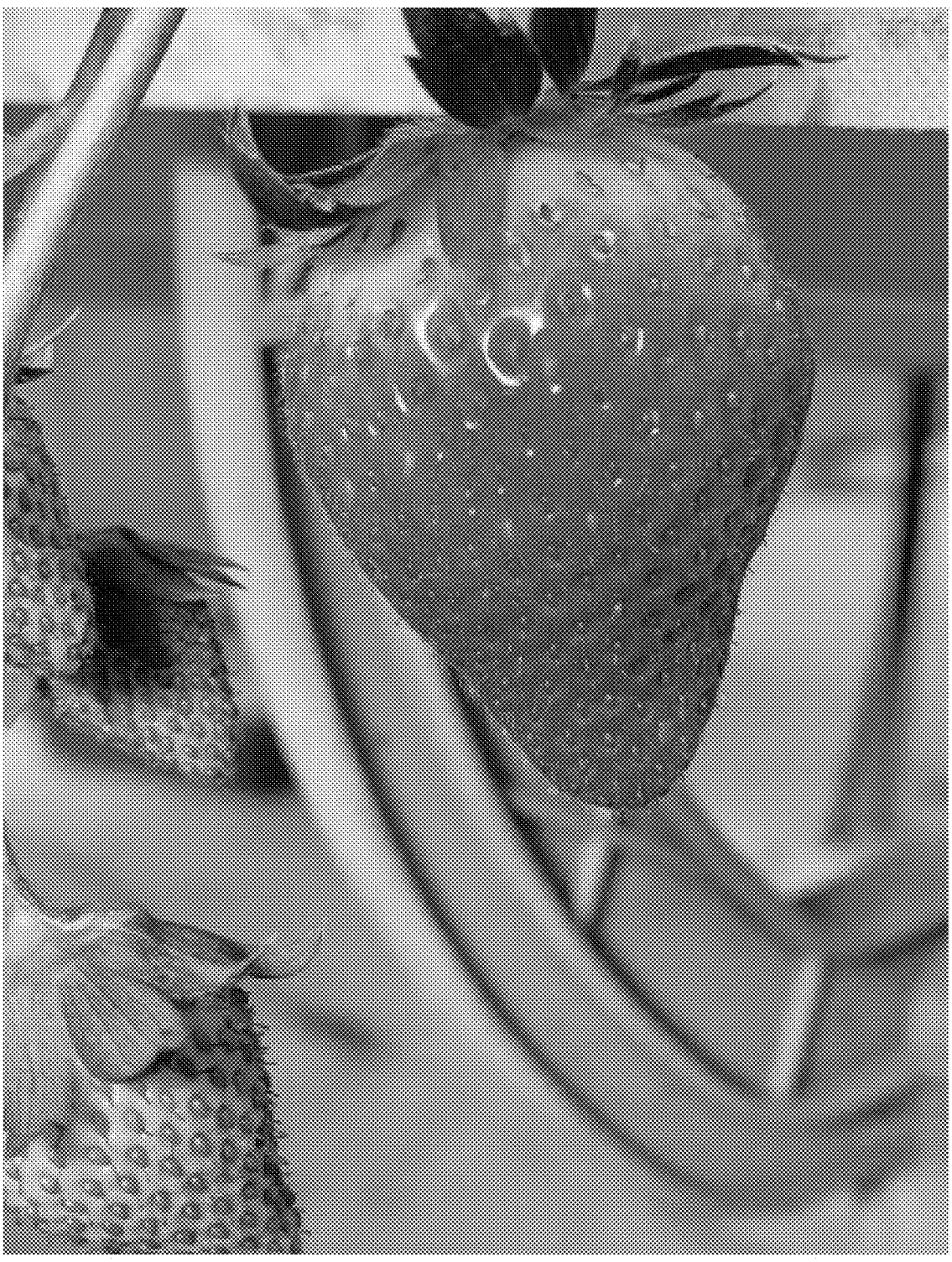
FIG. 1 illustrates whole fruit of variety 'Gold Berry'.
Figure 2:
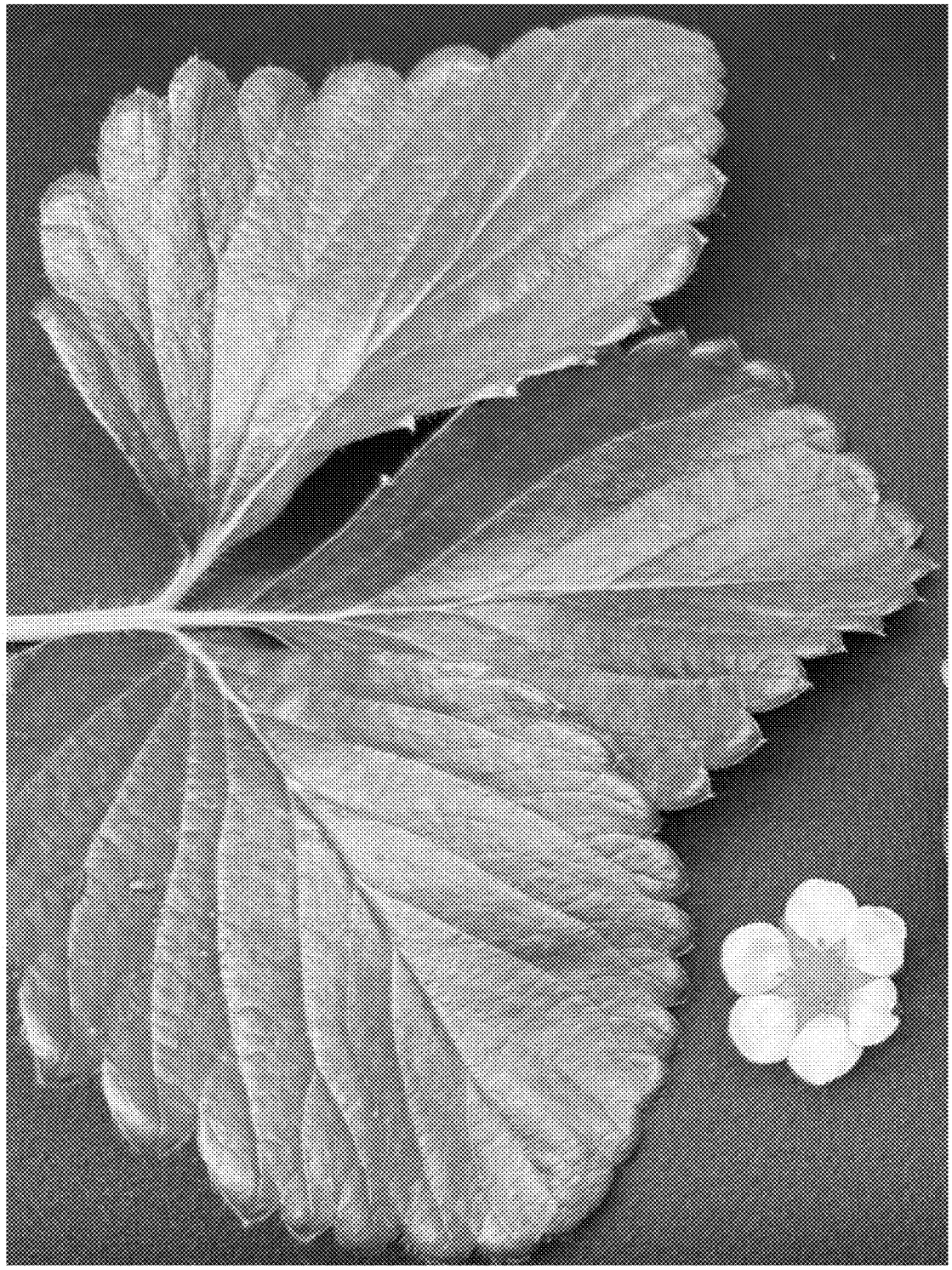
FIG. 2 illustrates a leaf of variety 'Gold Berry' with three leaflets and a single opened flower.
Figure 3:
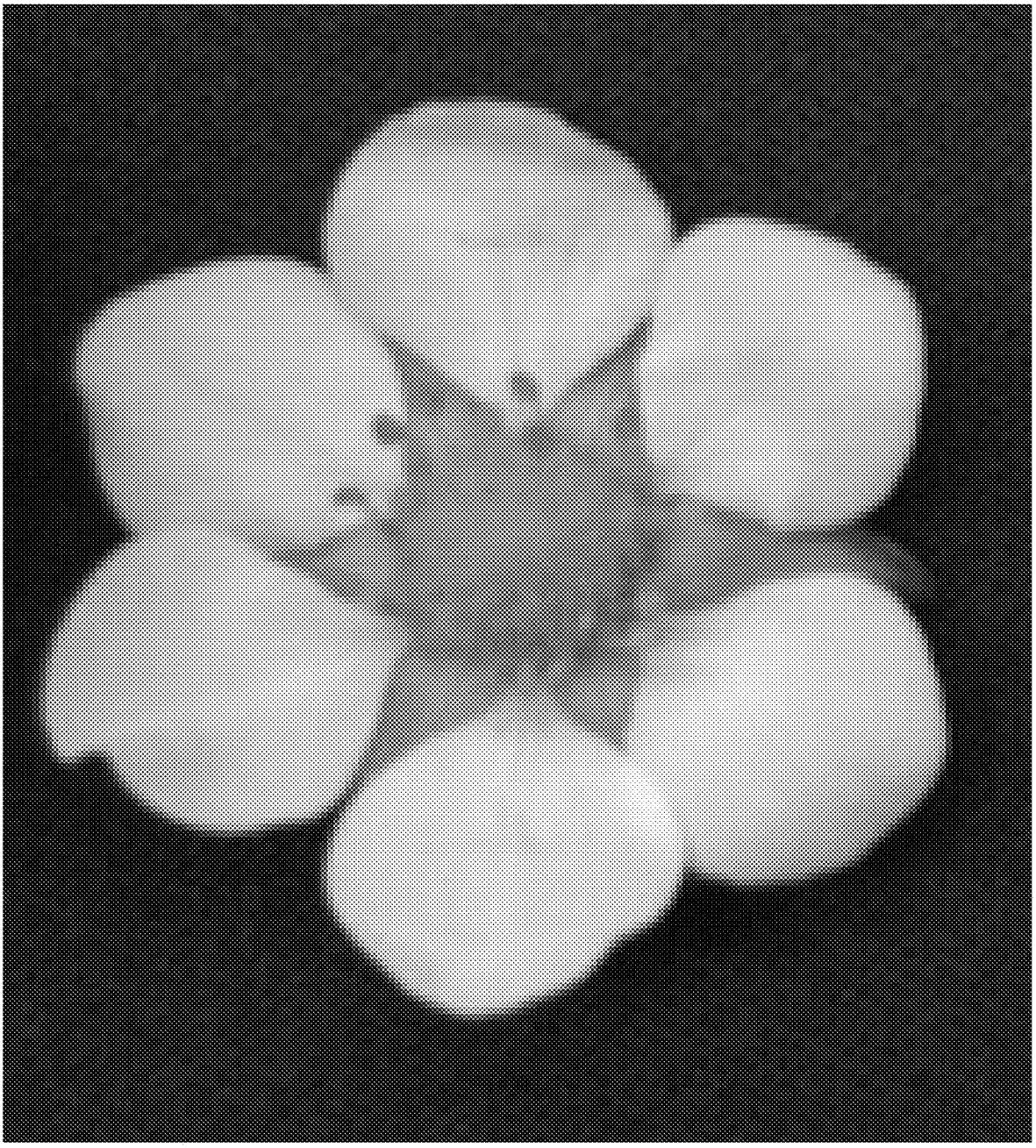
FIG. 3 illustrates a flower of variety 'Gold Berry'.
Figure 4:
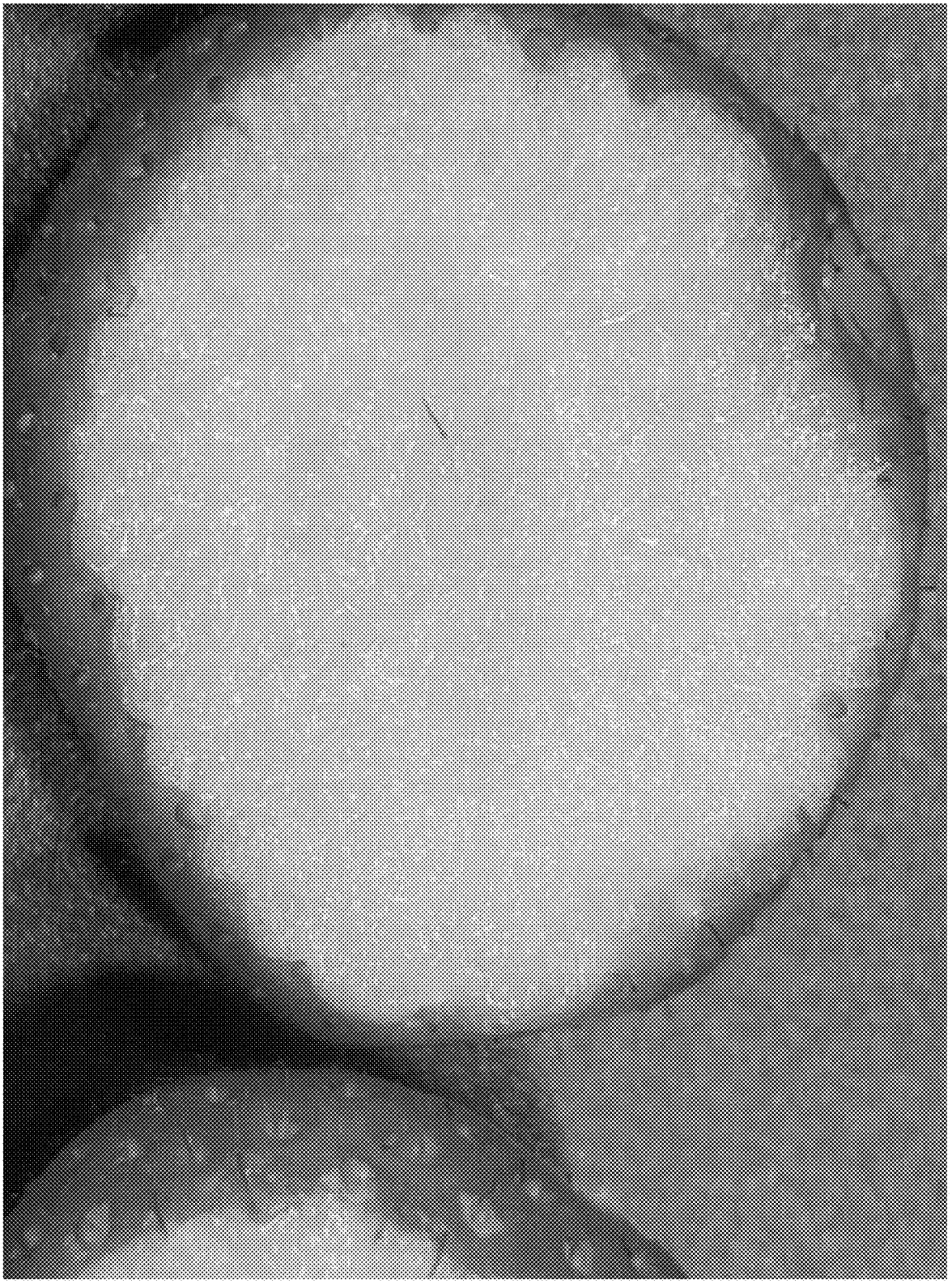
FIG. 4 illustrates a latitudinal cross-section of fruit of variety 'Gold Berry'.
Figure 5:
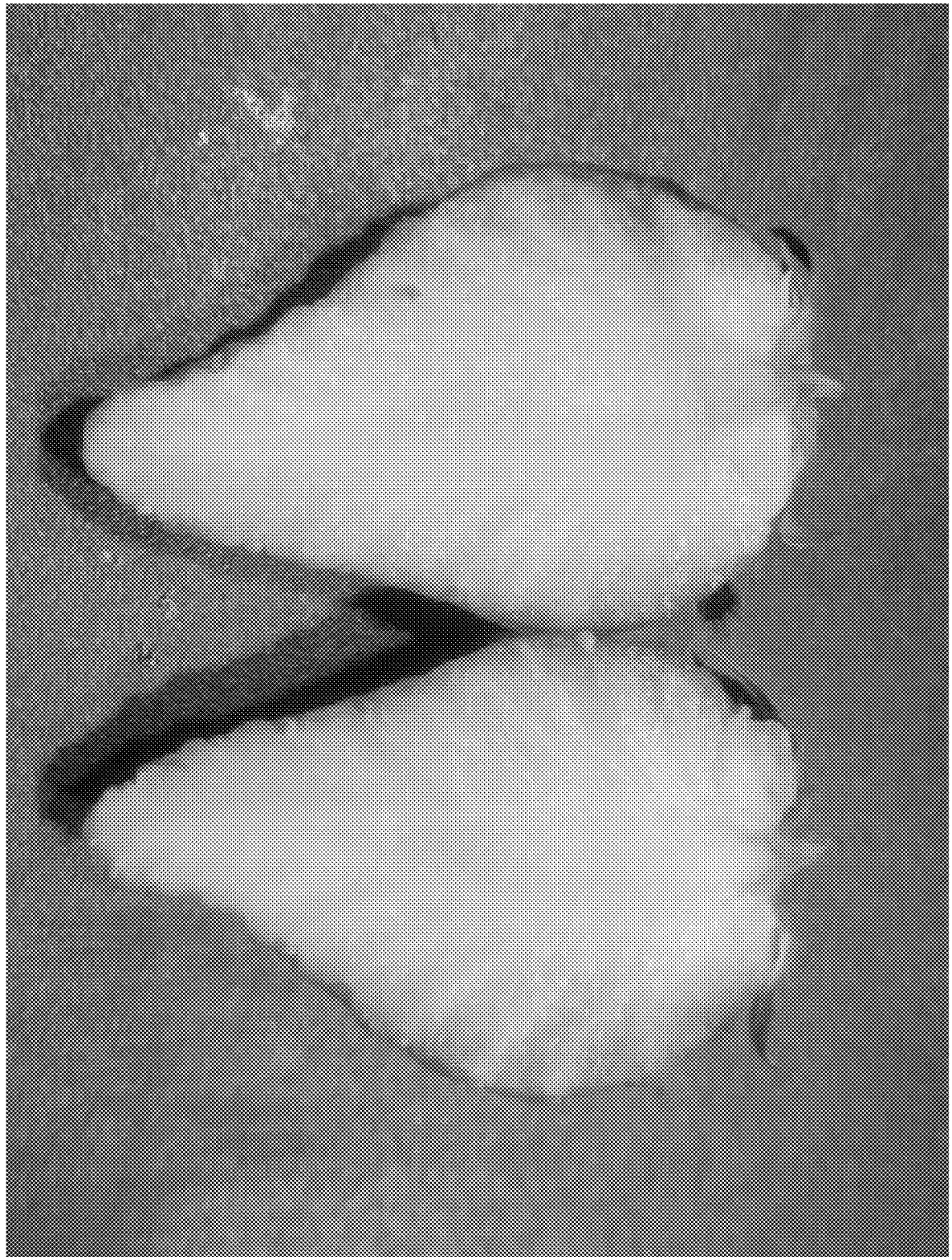
FIG. 5 illustrates a longitudinal cross-section of fruit of variety 'Gold Berry'.
Figure 6:
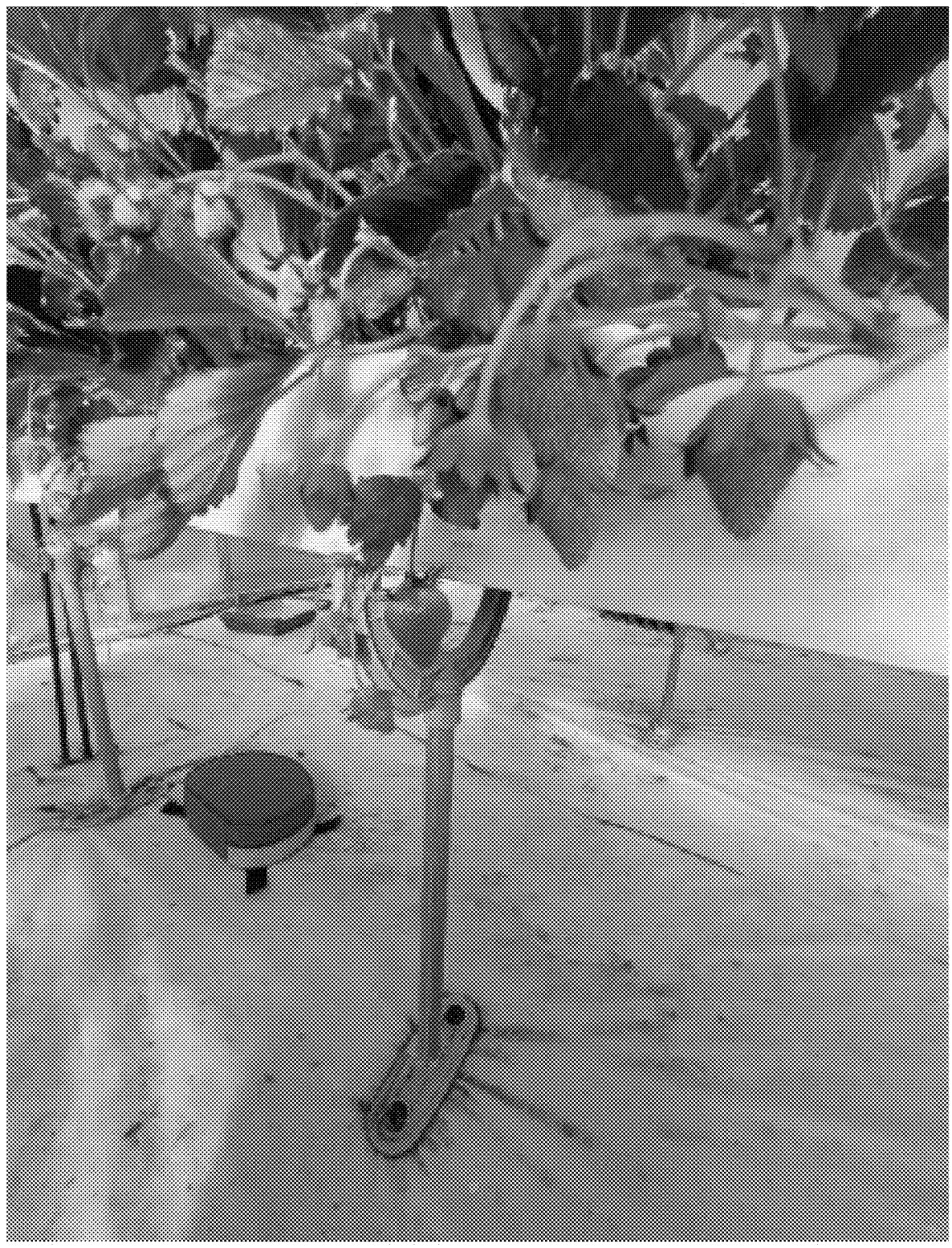
FIG. 6 illustrates 'Gold Berry' strawberry plants with fruit.

The following detailed descriptions set forth distinctive characteristics of 'Gold Berry'. The data which define these characteristics is based on observations taken in Dongsan-ri, Galsan-myeon, Hongseong-gun, Chungcheongnam-do, Republic of Korea, from 2020 to 2021. Color designations, color descriptions, and other phenotypical descriptions may deviate from the stated values and descriptions depending upon variation in environmental, seasonal, climatic, and cultural conditions. 'Gold Berry' has not been observed under all possible environmental conditions. The botanical description of 'Gold Berry' was taken from 3 month old plants. The indicated values represent averages calculated from measurements of several plants. Color references are primarily to The R.H.S. Colour Chart of The Royal Horticultural Society of London (R.H.S.) (2007 edition). Descriptive terminology follows the International Union for the Protection of New Varieties of Plants: Strawberry (UPOV Code: FRAGA), *Guidelines for the Conduct of Tests for Distinctness, Uniformity, and Stability,* 2023 Aug. 31 edition, unless where otherwise defined.

When 'Gold Berry' is compared to the female parent 'H2K-06' (unpatented), 'Gold Berry' produces conical-shaped fruit with higher sweetness and higher firmness.

When 'Gold Berry' is compared to the male parent 'STC-18-22' (unpatented), 'Gold Berry' produces larger fruit with higher yields.

When 'Gold Berry' is compared to the commercial variety, 'Seolhyang', the following distinctions are observed:

TABLE 1

'Gold Berry' compared to commercial variety, 'Seolhyang.'

| Trait | Gold Berry | Seolhyang |
|---|---|---|
| Fruit skin | Hard-skinned; durable | Semi-soft-skinned |
| Leaf color | Dark Green: RHS 138A-138B | Dark Green |
| Fruit skin color | Orangish Red: RHS 44A | Medium red |
| Fruit flesh color | Yellowish Pink: RHS 170B, 167D, and 161A | Dark red |
| Plant height | 20-30 cm | 30-40 cm |
| Fruit weight | 16 g | 15 g |
| Number of leaves | Medium | Many |
| Fruit empty space | Little to none | Many |

Classification:
- *Genus and species.*—*Fragaria* x *ananassa.*
- *Common name.*—Strawberry
- *Denomination.*—'Gold Berry'.

Parentage:
- *Female parent.*—The proprietary variety 'H2K-06' (unpatented).
- *Male parent.*—The proprietary variety 'STC-18-22' (unpatented).

Plant:
- *Height.*—20-30 cm.
- *Diameter.*—35-45 cm.
- *Habit.*—Upright to semi-upright.

Terminal leaflets:
- *Length.*—12 cm.
- *Width.*—8 cm.
- *Shape.*—Oval.
- *Length/width ratio.*—1.5.
- *Color.*—RHS 138A-138B (moderate yellowish green color).
- *Leaflet margin type.*—Serrate to crenate.
- *Upper surface texture.*—Moderately smooth.
- *Lower surface texture.*—Moderately rough.
- *Apex shape.*—Acute.
- *Base shape.*—Conic.

Lateral leaflets:
- *Length.*—11 cm.
- *Width.*—7 cm.
- *Shape.*—Oval.
- *Color.*—RHS 138A-138B (moderate yellowish green color).

Leaves:
- *Rugosity.*—Weak.
- *Glossiness.*—Strong.

Petiole:
- *Length.*—18 cm.
- *Diameter.*—0.6 cm.
- *Color.*—RHS N144D (light yellowish green).
- *Surface texture.*—Rough.
- *Attitude of the hairs.*—Upwards.

Petiolule:
- *Average length.*—2 cm.
- *Surface texture.*—Rough.
- *Color.*—N144D (light green).

Stolon:
- *Average number of daughter plants per square foot.*—30.
- *Runner length.*—45 cm.
- *Color.*—N144D (light green).

Stipule:
- *Average size.*—4 cm.
- *Shape.*—Ochreate.

*Intensity of anthocyanin coloration.*—None to very little coloration.
*Color.*—146D (green).

Inflorescence:
*Flower diameter.*—3.8 cm.
*Number of petals per flower.*—5-6.
*Petal color upper surface.*—RHS 193C (pale yellowish green)-194C (yellowish grey).
*Petal color lower surface.*—RHS 193C (pale yellowish green)-194C (yellowish grey).
*Petal length.*—0.8-1.2 cm.
*Petal width.*—0.6 cm
*Number of sepals per flower.*—12-14.
*Sepal length.*—1.2 cm.
*Sepal width.*—0.3 cm.
*Sepal color upper surface.*—RHS 144A (strong yellowish green).
*Sepal color lower surface.*—RHS 144A (strong yellowish green).
*Position in relation to foliage.*—Slightly above.
*Date of beginning flowering.*—October-November.
*Length of time flowering season.*—8 months.
*Flower petal shape and arrangement.*—Touching.
*Size of calyx in relation to the corolla.*—Same size.
*Presence of stamens.*—Yes.
*Number of stamens per flower.*—12.

Fruit:
*Length.*—5 cm.
*Width.*—3.8 cm.
*Length/width ratio.*—0.76 cm.
*Fruit weight.*—16 g.
*Predominant fruit shape.*—Conical.
*Fruit skin color.*—RHS 44A (vivid red).
*Color of achene.*—RHS 175C (dark reddish orange).
*Average number of achenes per berry.*—150.
*Color of flesh.*—RHS 170B (moderate orange), 167D (moderate orangish yellow), and 161A (moderate yellow).
*Color of core.*—RHS 166D (moderate orange).
*Distribution of flesh color.*—Solid.
*Harvest interval.*—Winter season.
*Brix level.*—11.1°.
*Fruit yield.*—500 g per plant.
*Fruit taste.*—Sweet.
*Fruit bearing.*—June bearing.
*Fruit shape at apex end.*—Acute, rounded.
*Fruit shape at calyx end.*—Obtuse, rounded.
*Position of fruit achenes.*—Slightly below surface.
*Fruit width band without achenes at calyx end.*—Absent or very narrow.
*Position of the fruit calyx attachment.*—Level with fruit.
*Attitude of fruit sepals.*—Upwards.
*Month of beginning fruit ripening when at least 50% of the fruits have ripened.*—December.
*Shipping quality.*—Good.
*Storage life.*—10 days.
*Market use.*—Human consumption.

Plant:
*Disease resistance.*—Weak to powdery mildew (*Erysiphe cruciferarum* Opiz ex L.).
*Plant hardiness zone.*—Not determined.
*Heat/cold resistance.*—Not determined.

The invention claimed is:

1. A new and distinct variety of strawberry plant named 'Gold Berry' as shown and described herein.

* * * * *